(12) United States Patent
Smith et al.

(10) Patent No.: US 8,920,394 B2
(45) Date of Patent: Dec. 30, 2014

(54) SUCTION CANISTER LINER AND SYSTEM

(71) Applicant: Dornoch Medical Systems Inc., Riverside, MO (US)

(72) Inventors: Larry C. Smith, Shawnee, KS (US); Craig B. Schmidt, Lenexa, KS (US)

(73) Assignee: Dornoch Medical Systems, Inc., Riverside, MO (US)

( * ) Notice: Subject to any disclaimer, the term of this patent is extended or adjusted under 35 U.S.C. 154(b) by 0 days.

(21) Appl. No.: 13/719,354

(22) Filed: Dec. 19, 2012

(65) Prior Publication Data

US 2014/0171887 A1 Jun. 19, 2014

(51) Int. Cl.
*A61M 1/00* (2006.01)

(52) U.S. Cl.
CPC .................................. *A61M 1/0001* (2013.01)
USPC ........................... 604/319; 604/317; 604/320

(58) Field of Classification Search
CPC ............................ A61M 1/001; A61M 1/0001
USPC .......... 604/317–320, 540, 541; 210/130, 136; 134/43–201
See application file for complete search history.

(56) References Cited

U.S. PATENT DOCUMENTS

| | | |
|---|---|---|
| 3,915,189 A | 10/1975 | Holbrook et al. |
| 4,275,732 A | 6/1981 | Gereg |
| 4,346,711 A | 8/1982 | Agdanowski et al. |
| 4,384,580 A | 5/1983 | Leviton |
| 4,392,860 A | 7/1983 | Huck et al. |
| 4,419,093 A | 12/1983 | Deaton |
| 4,455,140 A | 6/1984 | Joslin |
| 4,460,361 A | 7/1984 | Nichols |
| 4,653,518 A | 3/1987 | Adachi |
| 5,470,324 A | 11/1995 | Cook et al. |
| 5,620,428 A | 4/1997 | Hand et al. |
| 5,683,371 A | 11/1997 | Hand et al. |
| 5,688,255 A | 11/1997 | Hand et al. |
| 5,741,237 A | 4/1998 | Walker |
| 5,741,238 A | 4/1998 | Bradbury et al. |
| 5,776,118 A | 7/1998 | Seifert et al. |
| 5,776,260 A | 7/1998 | Dunn et al. |
| 5,792,126 A | 8/1998 | Tribastone et al. |
| 5,807,359 A | 9/1998 | Bemis et al. |
| 5,871,476 A | 2/1999 | Hand et al. |
| 5,885,240 A | 3/1999 | Bradbury et al. |
| 5,901,717 A | 5/1999 | Dunn et al. |
| 5,931,822 A | 8/1999 | Bemis et al. |
| 5,944,703 A | 8/1999 | Dixon et al. |
| 5,945,004 A | 8/1999 | Ohira et al. |

(Continued)

*Primary Examiner* — Leslie Deak
*Assistant Examiner* — Kai Weng
(74) *Attorney, Agent, or Firm* — Seager, Tufte & Wickhem, LLC

(57) ABSTRACT

A suction canister liner including a body portion having a sidewall and a bottom. An annular tapered sealing surface is positioned over the sidewall of the canister liner body portion to allow ease of loading and unloading. The annular tapered sealing surface has a top diameter and a bottom diameter, where the top diameter is greater than the bottom diameter. The canister liner may be placed within the interior of a canister. The canister sidewall includes a vacuum port adapted to communicate with a vacuum source. A lid having a patient port and a suction port engages and removably covers the open top end of the canister liner. The annular tapered sealing surface of the canister liner seals against the interior surface of the rim of the canister when a vacuum is applied to the canister interior through the vacuum port by the vacuum source.

18 Claims, 8 Drawing Sheets

(56) References Cited

U.S. PATENT DOCUMENTS

| | | | |
|---|---|---|---|
| 5,960,837 | A | 10/1999 | Cude |
| 5,975,096 | A | 11/1999 | Dunn et al. |
| 6,056,731 | A | 5/2000 | Koetke et al. |
| 6,152,902 | A * | 11/2000 | Christian et al. ............ 604/320 |
| D435,906 | S | 1/2001 | Wilkinson et al. |
| 6,261,276 | B1 | 7/2001 | Reitsma |
| 6,263,887 | B1 | 7/2001 | Dunn |
| 6,358,232 | B1 | 3/2002 | Hand et al. |
| 6,494,869 | B1 | 12/2002 | Hand et al. |
| 6,588,436 | B2 | 7/2003 | Dunn et al. |
| 6,626,877 | B2 | 9/2003 | Anderson et al. |
| 6,652,495 | B1 | 11/2003 | Walker |
| 6,672,477 | B2 | 1/2004 | Miller et al. |
| 6,673,055 | B2 | 1/2004 | Bemis et al. |
| 6,688,483 | B2 * | 2/2004 | Davis ............................ 220/276 |
| 6,688,487 | B2 * | 2/2004 | Oakes et al. ................... 220/788 |
| 6,776,175 | B2 | 8/2004 | Dunn et al. |
| 6,796,317 | B2 | 9/2004 | Dunn et al. |
| 6,893,425 | B2 | 5/2005 | Dunn et al. |
| 7,090,663 | B2 | 8/2006 | Dunn et al. |
| 7,115,115 | B2 | 10/2006 | Bemis et al. |
| 7,258,711 | B2 | 8/2007 | Dunn et al. |
| 7,497,340 | B2 | 3/2009 | Hershberger et al. |
| 7,585,292 | B2 | 9/2009 | Anderson et al. |
| 7,674,248 | B2 | 3/2010 | Anderson et al. |
| 7,879,228 | B2 | 2/2011 | Dunn et al. |
| 7,892,420 | B2 | 2/2011 | Dunn et al. |
| 8,025,173 | B2 | 9/2011 | Michaels |
| 8,292,857 | B2 | 10/2012 | Martini et al. |
| 2005/0004537 | A1 | 1/2005 | Dunn et al. |
| 2005/0010179 | A1 | 1/2005 | Dunn et al. |
| 2005/0139532 | A1 | 6/2005 | Hershberger et al. |
| 2005/0171495 | A1 | 8/2005 | Austin |
| 2005/0187529 | A1 | 8/2005 | Reasoner et al. |
| 2007/0135779 | A1 | 6/2007 | Lalomia et al. |
| 2008/0053539 | A1 | 3/2008 | Hershberger et al. |
| 2009/0005747 | A1 | 1/2009 | Michaels et al. |
| 2009/0012485 | A1 | 1/2009 | Michaels et al. |
| 2009/0159535 | A1 | 6/2009 | Hershberger et al. |
| 2010/0043910 | A1 * | 2/2010 | Szekely et al. ..................... 141/1 |
| 2012/0215187 | A1 * | 8/2012 | Tippet et al. ................. 604/319 |

* cited by examiner ary procedure, is connected to a source of vacuum via a hose or line. As illustrated in FIG. 4B by arrow 60, this causes the collar portion 36 and lip portion 38 of the canister liner to move inward, away from the rim 52 of the canister. The canister lid 54 is then installed on the top of the canister liner and canister in the direction of arrow 62.

SUCTION CANISTER LINER AND SYSTEM

FIELD OF THE INVENTION

The present invention relates generally to systems for collecting biological fluids during medical procedures and, in particular, to a disposable suction canister liner and system.

BACKGROUND

Biological fluids and other types of medical waste often must be collected during surgery or other medical procedures. This is typically accomplished using a suction canister where a suction port on the canister lid is connected to a source of vacuum or suction via a hose or line. As a result, a vacuum is drawn on the interior of the canister. A second hose or line is connected to a patient port on the canister lid and is used to collect medical waste in the form of fluids and solids from the patient, which is stored in the canister.

After collection, the medical waste, and contaminated collection components, such as canister lids, canisters and the like, must be disposed of in accordance with rules and regulations imposed by various government and regulatory organizations. Such medical waste is called "red bag waste" and the associated procedures for disposal may be quite costly. As a result, it is desirable to limit the number of components that must be disposed of as red bag waste.

In view of the above, medical waste disposal systems and methods have been developed where a reusable medical waste collection canister is drained, rinsed and disinfected after a medical procedure, thereby eliminating red bag waste. An example of such a system is provided in commonly assigned U.S. Pat. Nos. 6,588,436 and 6,776,175, both to Dunn et al., the contents of which are hereby incorporated by reference.

While the systems of the Dunn et al. '436 and '175 patents perform well, in certain situations it may be more economical to use a disposable canister instead of a reusable canister. For example, a disposable canister avoids the equipment, time and cost required to sanitize reusable canisters. As noted above, however, a disposable canister that is contaminated with medical waste after use must be disposed of as red bag waste, which is undesirable. A need therefore exists for a disposable canister liner that is easy to use and that may be drained and rinsed of any bio-burden after use and then disposed of as "white bag waste."

DETAILED DESCRIPTION OF EMBODIMENTS

Figure 1:
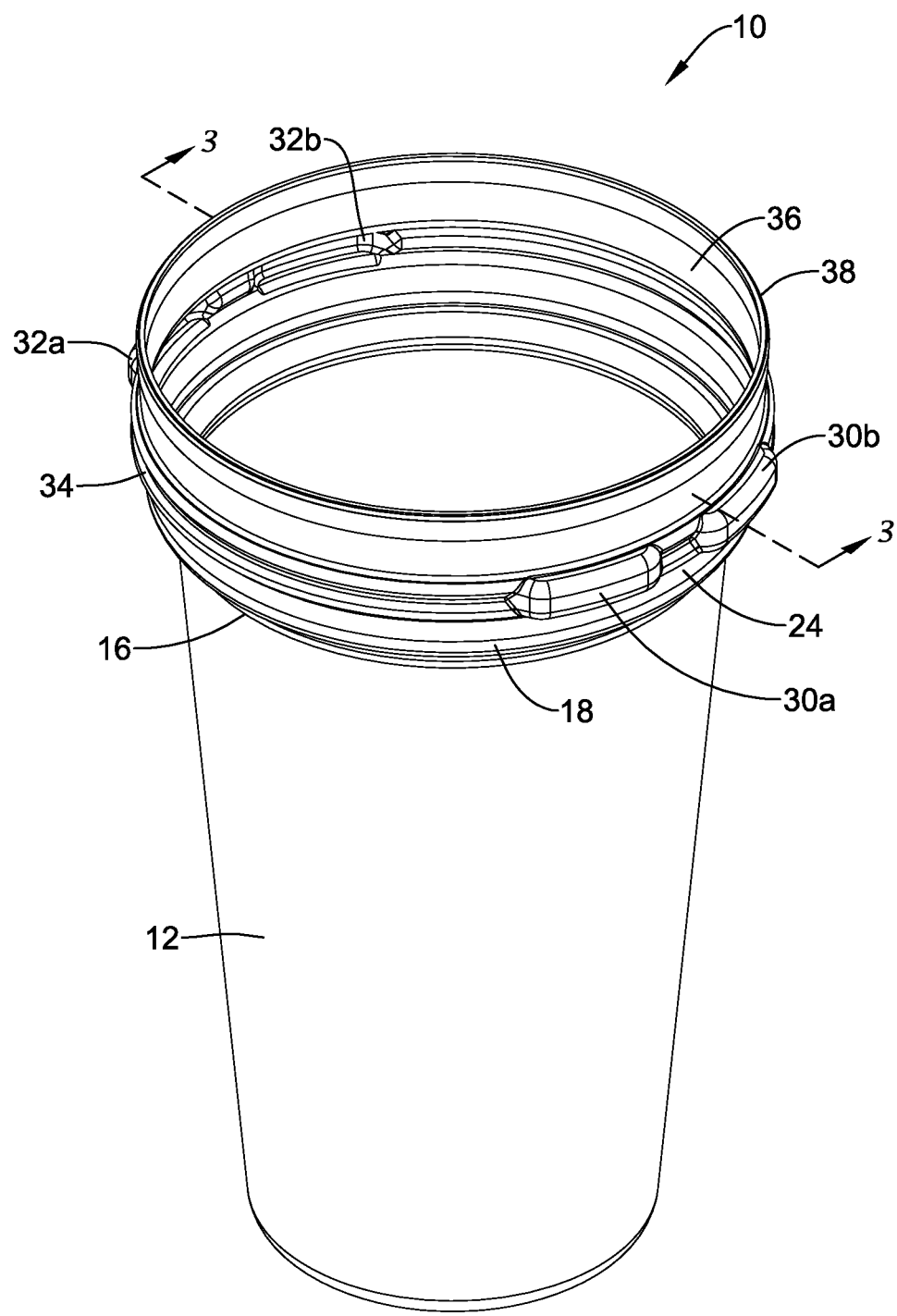
FIG. 1 is a perspective view of an embodiment of the disposable canister liner of the invention.
Figure 2:
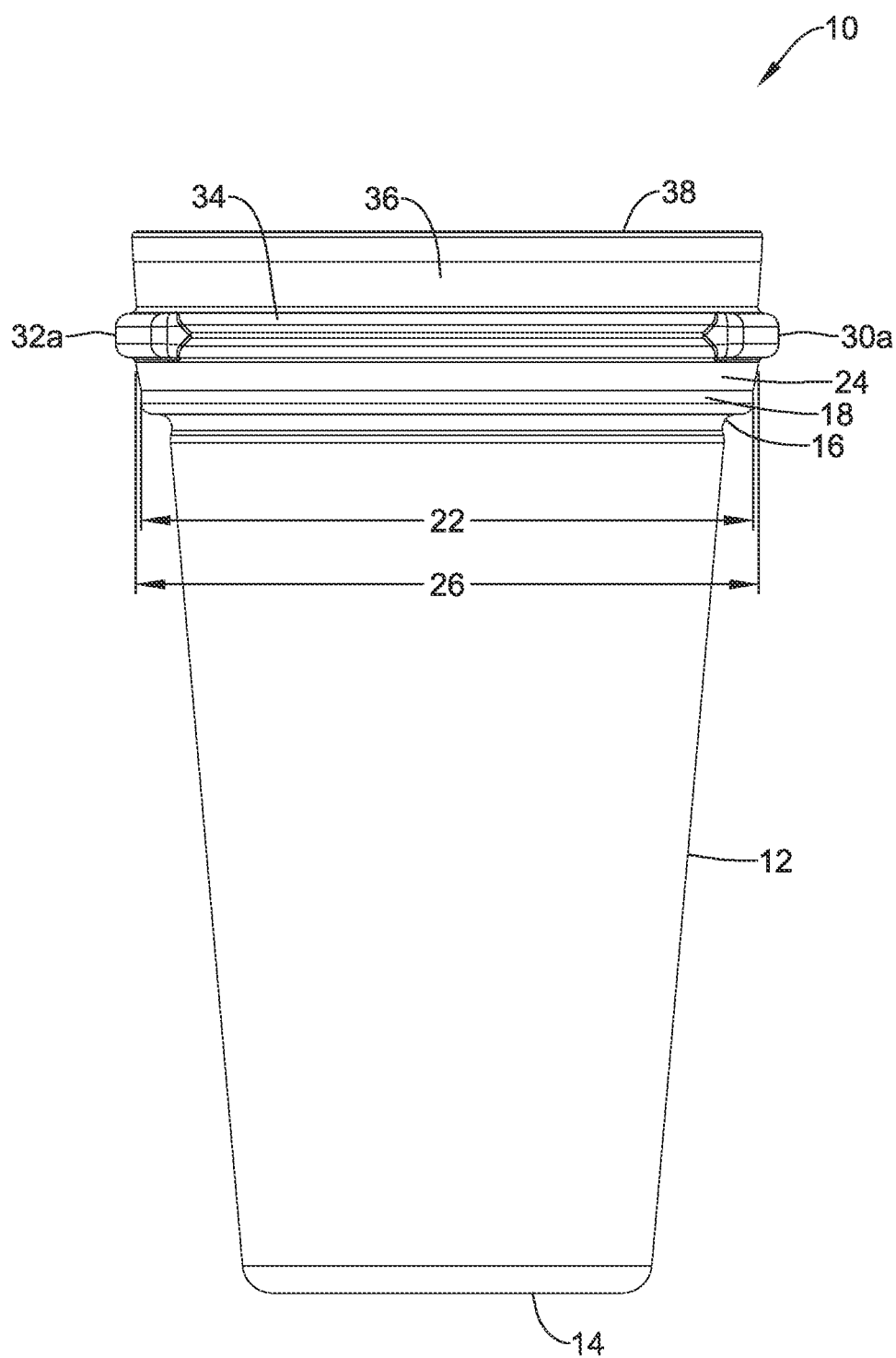
FIG. 2 is a side elevational view of the canister liner of FIG. 1.
Figure 3:
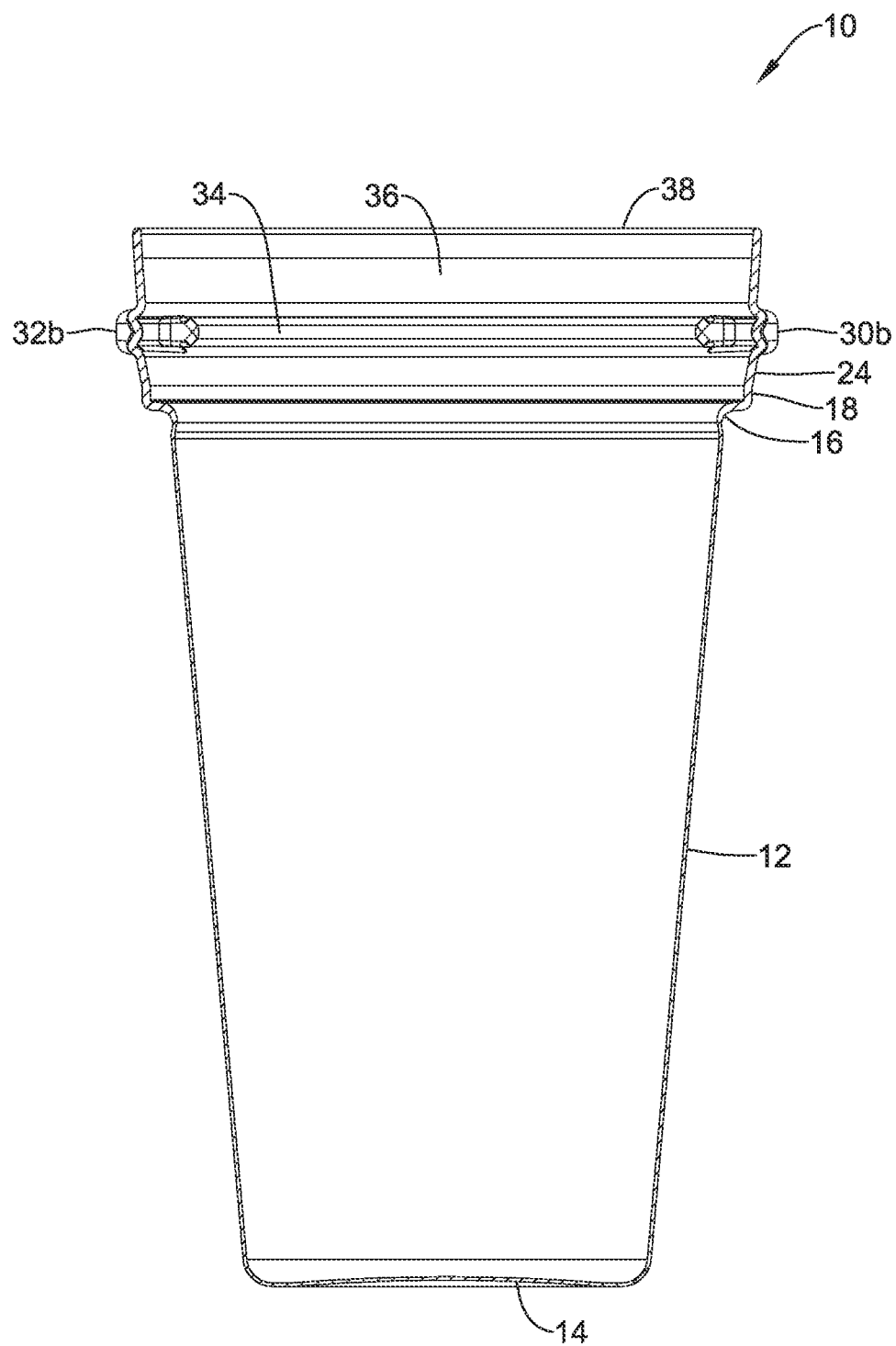
FIG. 3 is cross-sectional view of the canister liner of FIGS. 1 and 2, taken along lines 3-3 of FIG. 1.

An embodiment of the suction canister liner of the present invention is indicated in general at 10 in FIGS. 1-3. The canister liner includes a tapered, cylindrical body portion, formed by continuous sidewall 12. The cylindrical body portion also includes a closed bottom, illustrated at 14 in FIG. 3. The canister liner is preferably disposable and constructed from a plastic material such as high density polyethylene (HDPE) or polyethylene terephthalate (PET). The canister liner 10 is preferably formed as a single piece and may be made, for example, by an extrusion blow molding process.

The thickness of the sidewalls and bottom of the canister liner must be such as to provide the canister liner with sufficient rigidity to remain open and not buckle or otherwise flop over during washing, and to also provide sealing and release when installed in and removed from a canister in the manner described below. As an example only, the canister liner may be sized to hold 2400 mL of liquid medical waste with a thickness of sidewall 12 and a thickness of bottom 14 that are both preferably approximately 0.06 inches.

As illustrated in FIGS. 1-3, an annular recess portion 16 is formed at the top edge of continuous sidewall 12. Above the annular recess portion is an annular transition portion 18. An annular tapered sealing surface 24 is positioned above the transition portion 18 and has a bottom diameter indicated by arrows 22 in FIG. 2 and a top diameter indicated by arrows 26. As an example only, continuing with a canister liner that is sized to hold 2400 mL of liquid medical waste, dimension 22 may be approximately 5.92 inches while dimension 26 may be approximately 6.03 inches.

As best shown in FIG. 1, a first pair of protrusions 30a and 30b are positioned on one side of the canister liner above the tapered sealing surface. A second pair of protrusions 32a and 32b are positioned on an opposite side of the liner, also above the tapered sealing surface. Running between each of the protrusions, and also bordering the upper edge of the tapered sealing surface is step portion 34. A circumferential collar portion 36 is positioned above the protrusions 30a, 30b, 32a and 32b and step portion 34. The top of the collar portion 36 is provided with circumferential lip portion 38, which encircles the open top of the canister liner.

In use, the suction canister liner 10 of FIGS. 1-3 is installed within a reusable canister, such as the one disclosed in commonly assigned U.S. Pat. No. 6,796,317 to Dunn et al., the contents of which are hereby incorporated by reference. The liner may alternatively be installed within another type of holder. A canister lid, having suction and patient ports, is then installed on the lip portion 38 of the canister liner. Details of this process will now be described with respect to FIGS. 4A-6.

Figure 4A:
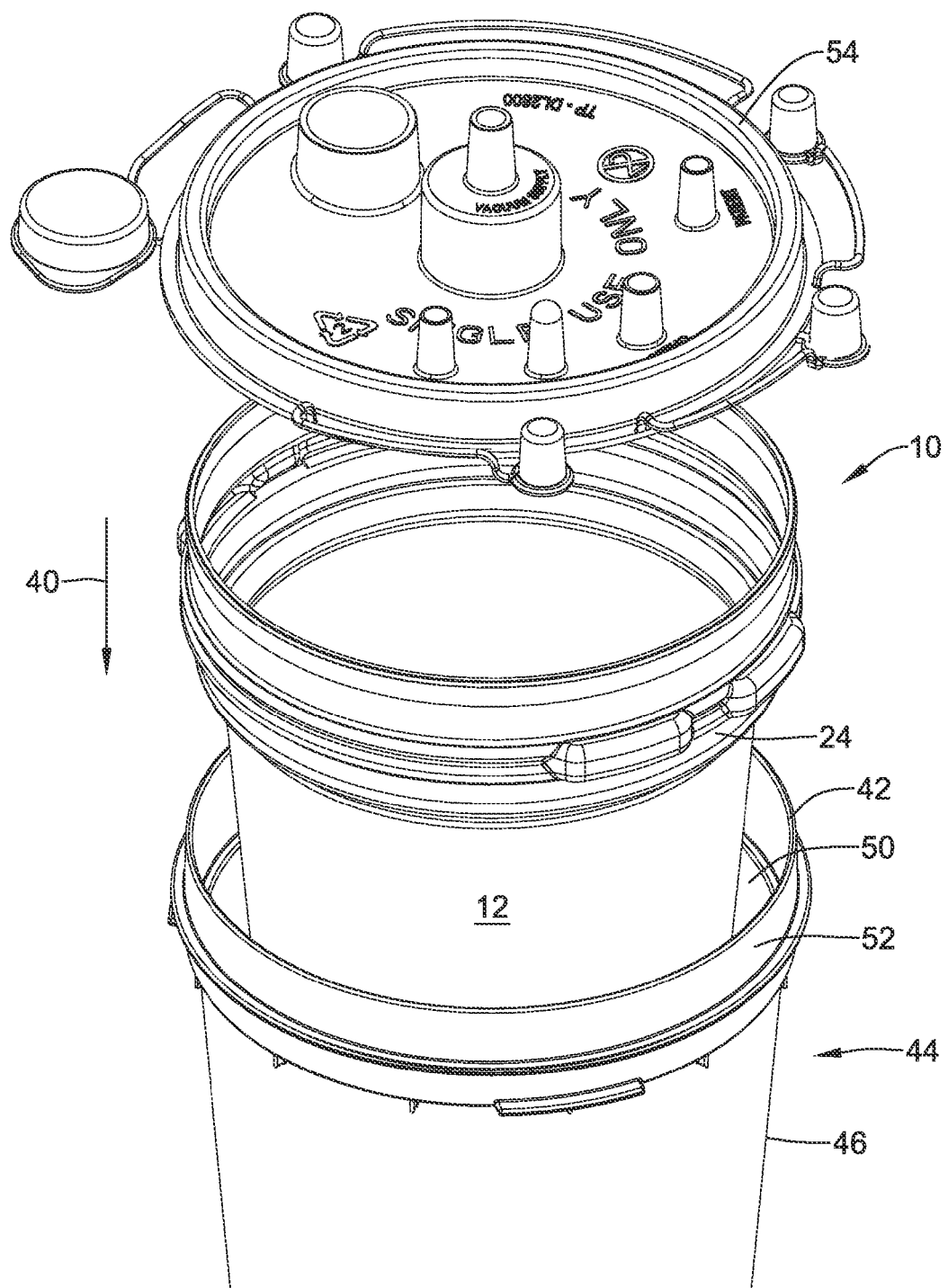
FIGS. 4A-4C are partial perspective views illustrating installation of the canister liner of FIGS. 1-3 and a disposable lid in a reusable canister in an embodiment of the system of the present invention.

As illustrated in FIG. 4A by arrow 40, the body portion of the disposable canister liner 10, including the continuous sidewall 12 and bottom, are inserted through the open top 42 of a canister, indicated in general at 44. Similar to the canister liner 10, the canister 44 includes a continuous sidewall 46 and a closed bottom (indicated at 48 in FIGS. 5 and 6) which define the canister interior 50 (also indicated in FIGS. 5 and 6). A circumferential rim 52 is positioned on the top of the canister sidewall 46. The canister 44 is preferably reusable and, as an example only, it may be molded from transparent polycarbonate plastic. A lid 54 is also provided and, as explained in greater detail below, is ultimately installed to close the open top of the canister liner.

When the body portion of the canister liner is entirely enclosed within the interior 50 of the canister, the tapered sealing surface 24 of the liner contacts the rim 52 of the canister.

Figure 4B:
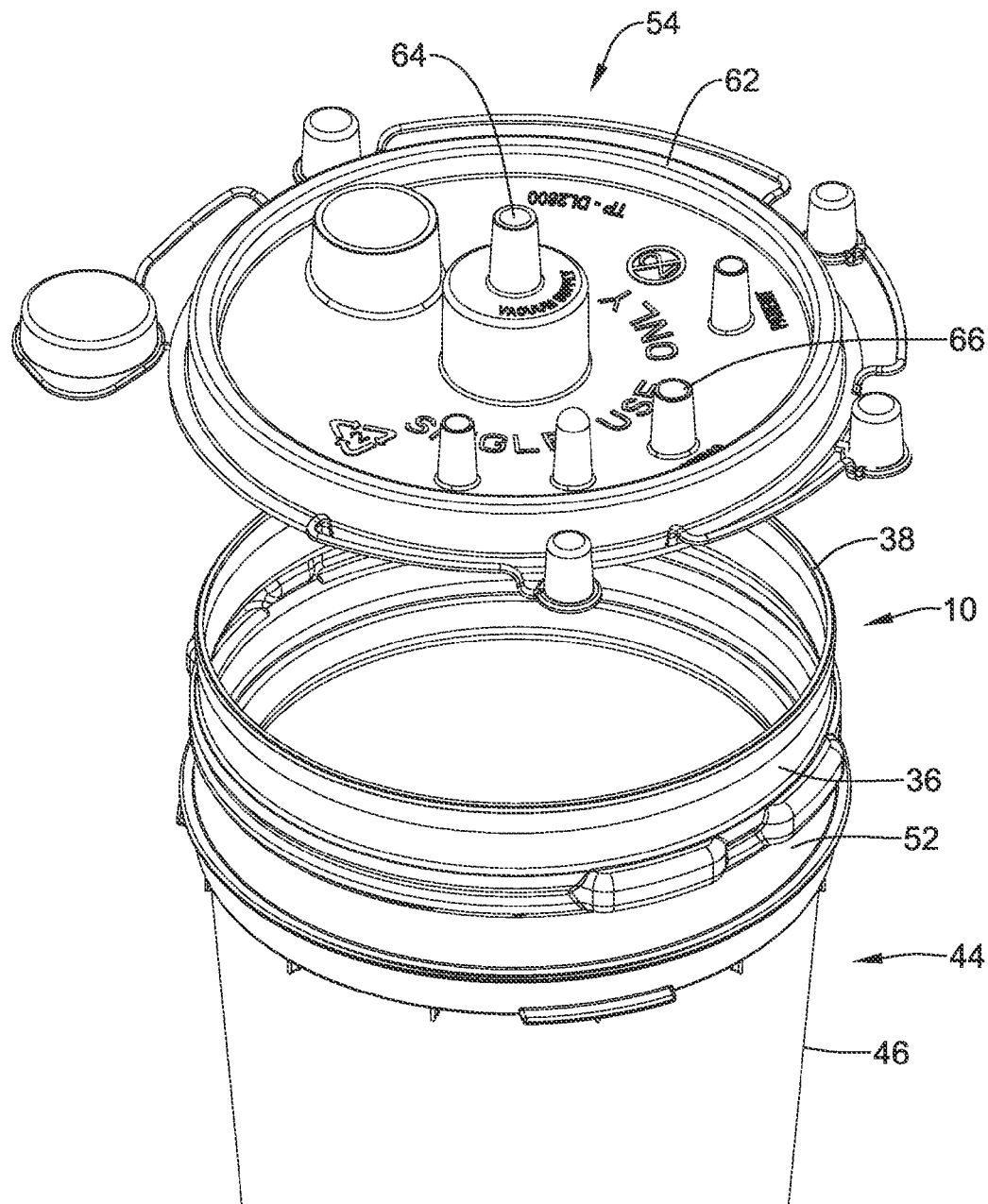
Figure 4C:
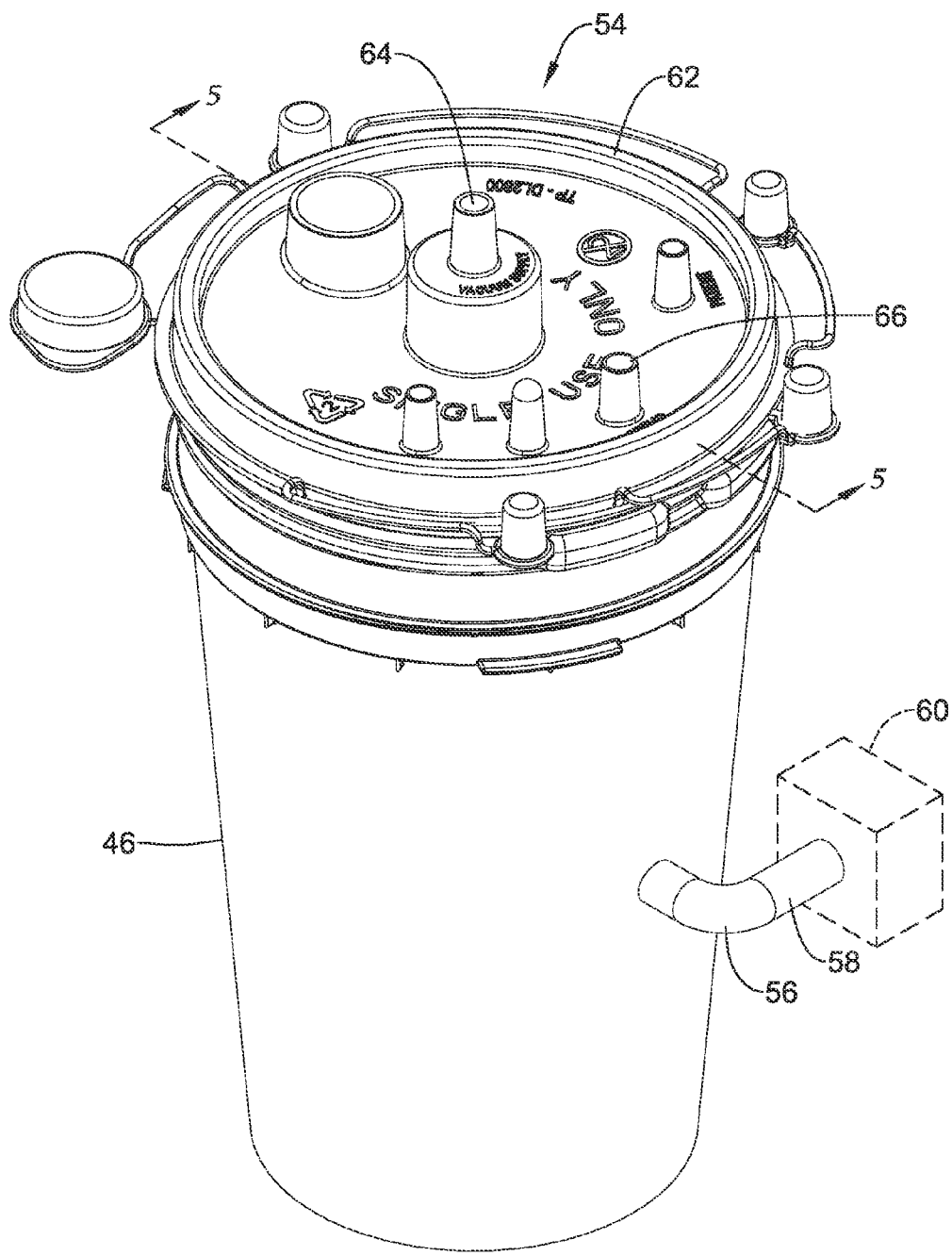
Figure 5:
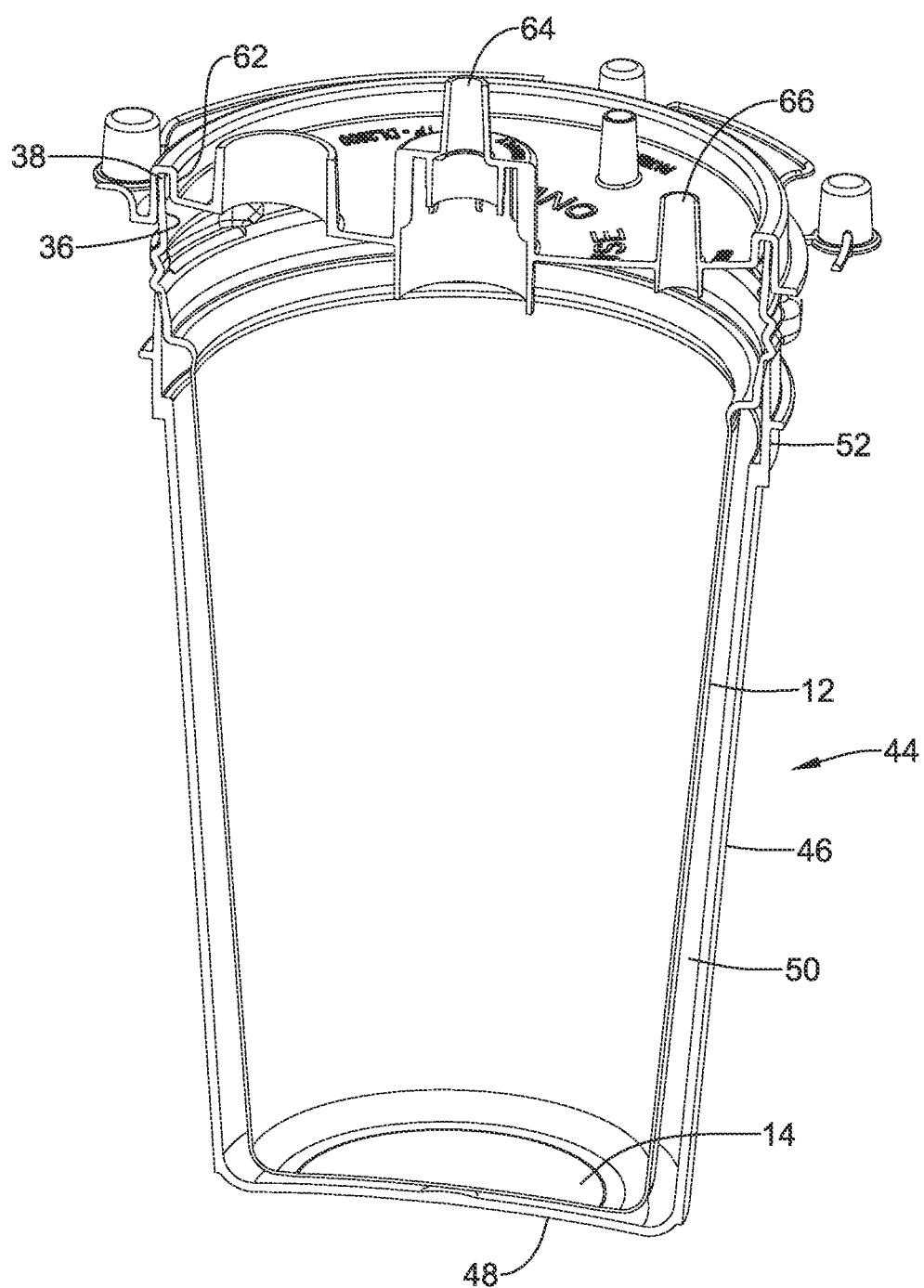
FIG. 5 is a perspective cross sectional view of the assembled canister liner, lid and canister of FIG. 4C taken along line 5-5 of FIG. 4C.
Figure 6:
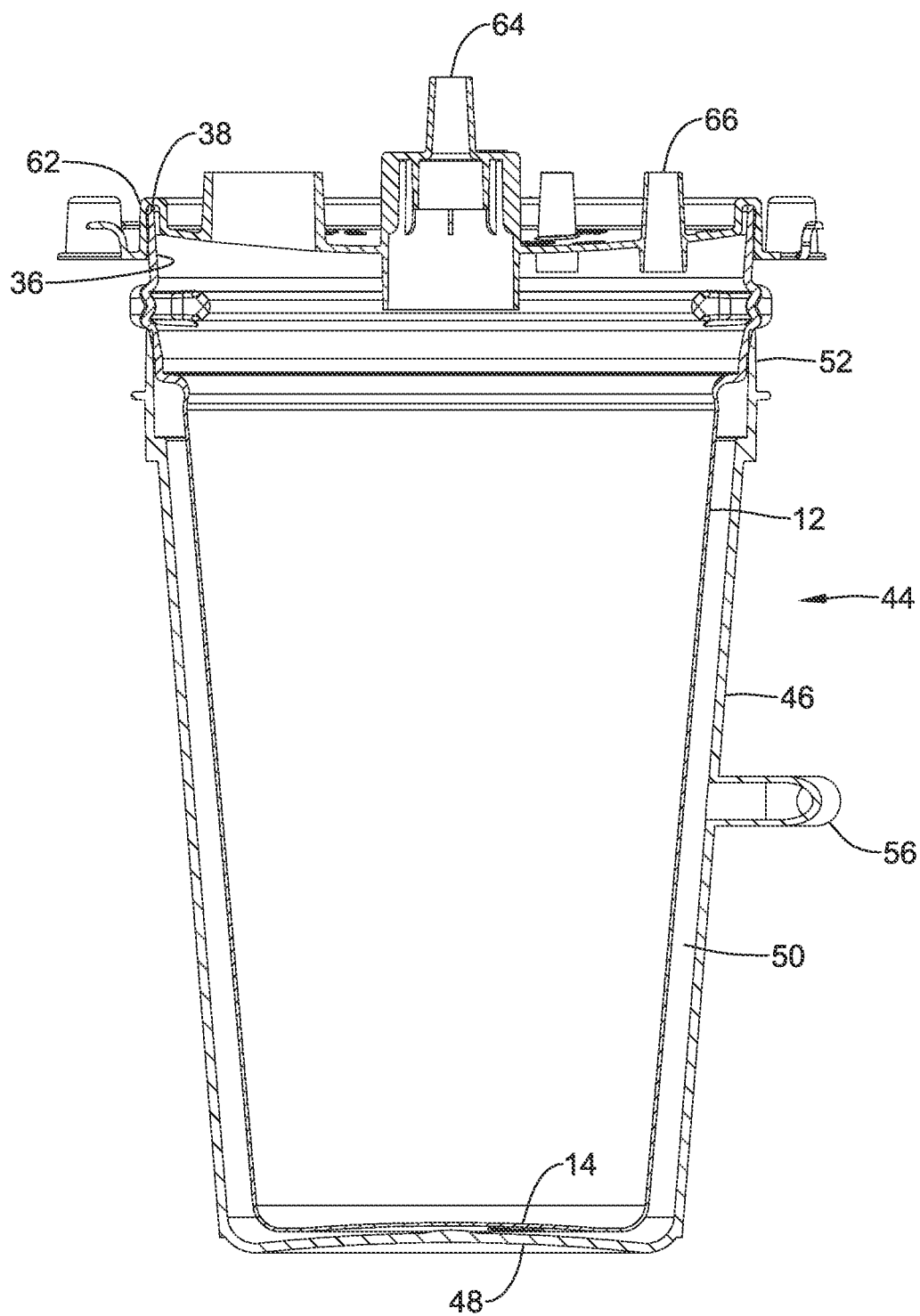
FIG. 6 is a side elevational cross sectional view of the assembled canister liner, lid and canister of FIG. 5.

As illustrated in FIGS. 4C and 6, the sidewall 46 of the canister is provided with a vacuum port 56 that, when the canister is in use to collect medical waste during a mediprocedure, is connected via line 58 to a vacuum source, indicated in phantom at 60. As an example only, the vacuum source 60 may be a hospital vacuum system or a vacuum pump. With reference to FIGS. 5 and 6, when the vacuum source 60 is activated, a vacuum or suction occurs in the interior 50 of the canister, between the continuous sidewall 12 of the canister liner and the continuous sidewall 46 of the canister, and between the bottom 14 of the canister liner and the bottom 48 of the canister. This causes the canister liner to be pulled further down into the interior of the canister through a distance, for example, of approximately 0.20 inches. The taper of the tapered sealing surface 24 of the canister liner causes the sealing surface of the canister liner to compress slightly, via a wedging action, and a circumferential seal to be achieved between the tapered sealing surface 24 of the canister liner and the interior surface of the rim 52 of the canister. The protrusions 30*a*, 30*b*, 32*a* and 32*b* and step portion 34 of the canister liner, located at the top of the tapered sealing surface 24 provide controlled sealing surface geometry and a sure stop which positions the canister liner correctly within the outer canister for use, as illustrated in FIGS. 4B, 5 and 6.

As illustrated in FIGS. 4B-6, the lid 54 features a circumferential channel 62 that receives the circumferential collar portion 36 and the circumferential lip portion 38 of the canister liner in a sealing fashion. The lid, which is preferably constructed from plastic and is disposable, features a suction port 64 and at least one patient port 66, both of which are in fluid communication with the interior of the canister liner when the lid is positioned on the canister liner (as illustrated in FIGS. 4C-6). As is known in the art, during a medical procedure, the suction port 64 is connected to a vacuum source (60 in FIG. 4C) via a hose or line, and a second hose or line is connected to a patient port 66 and is used to collect medical waste from the patient, which is stored in the canister liner.

During fluid collection, the seal between the canister liner sealing surface 24 and the interior surface of the rim 52 of the canister remains intact, which makes certain that the vacuum is applied equally to the inner and outer surfaces of the liner. This prevents the semi-rigid, soft walled canister liner from collapsing.

After a medical procedure, when the collection of medical waste is complete, the suction port 64 of the lid 54 and the vacuum port 56 of the canister are disconnected from the vacuum source. As a result, the tapered sealing surface 24 of the canister liner applies a force on the rim 52 of the canister which automatically lifts the canister liner from the sealed positioned in the canister. This lifting unseals the canister liner from the canister and positions it in a resting, uncompressed position on the top edge of the rim 52 of the canister. This allows the canister liner to be easily lifted away from the canister. The liner may then be drained and rinsed of any bio-burden for disposal as white bag trash. The protrusions 30*a*, 30*b*, 32*a* and 32*b* permit the canister liner to be cleaned in the systems of previously referenced and commonly assigned U.S. Pat. Nos. 6,588,436 and 6,776,175, both to Dunn et al.

Another benefit of the canister liner of FIGS. 1-6 is that the tapered seal edge geometry provides automatic centering of the canister liner within the canister, which in turn provides for ease of loading of the liner. In addition, the canister liner permits a normal suction canister lid to be used, in contrast to requiring the manufacture and purchase of a custom lid.

In view of the above, the canister liner described and illustrated in FIGS. 1-6 provides easy loading as well as automatic unloading of the canister liner from the canister. This makes the canister liner very easy to use.

While the preferred embodiments of the invention have been shown and described, it will be apparent to those skilled in the art that changes and modifications may be made therein without departing from the spirit of the invention, the scope of which is defined by the appended claims.

What is claimed is:

1. A suction canister liner comprising:
    a) a cylindrical body portion having a sidewall and a bottom;
    b) an annular tapered sealing surface positioned over the sidewall of said body portion;
    c) said annular tapered sealing surface having a top diameter and a bottom diameter, where the top diameter is greater than the bottom diameter; and
    d) a plurality of outwardly extending protrusions positioned above the annular tapered sealing surface and extending radially from the suction canister liner; and
    wherein the plurality of outwardly extending protrusions are configured to contact an upper rim of an outer canister when the suction canister liner is positioned within the outer canister.

2. The suction canister liner of claim 1 further comprising an annular recess portion positioned between the sidewall and the annular tapered sealing surface.

3. The suction canister liner of claim 2 further comprising an annular transition portion positioned between the annular recess portion and the annular tapered sealing surface.

4. The suction canister liner of claim 1 further comprising a circumferential collar portion positioned above the annular tapered sealing surface.

5. The suction canister liner of claim 4 further comprising a circumferential lip portion positioned at a top edge of the circumferential collar portion.

6. The suction canister liner of claim 4 wherein the plurality of protrusions are positioned between the circumferential collar portion and the annular tapered sealing surface.

7. The suction canister liner of claim 6 further comprising a step portion running between the plurality of protrusions.

8. The suction canister liner of claim 4 further comprising a step portion positioned between the circumferential collar portion and the annular tapered sealing surface.

9. The suction canister liner of claim 1 further comprising a step portion positioned over the annular tapered sealing surface.

10. A system for collecting medical waste fluids comprising:
    a) a canister having a canister sidewall and a canister bottom defining a canister interior and a circumferential rim having an interior surface, said circumferential rim positioned over said canister sidewall, said canister sidewall including a vacuum port adapted to communicate with a vacuum source;
    b) a canister liner having an open top end, a liner sidewall and a liner bottom with an annular tapered sealing surface positioned over the liner sidewall and a plurality of outwardly extending protrusions positioned above the annular tapered sealing surface,
    c) a lid having a patient port and a suction port, said lid removably covering the open top end of the canister liner and positioned above and free from contact with said plurality of outwardly extending protrusions; and
    d) said annular tapered sealing surface of the canister liner sealing against the interior surface of the rim of the canister when a vacuum is applied to the canister interior through the vacuum port by the vacuum source; and
    e) said annular tapered sealing surface of the canister liner automatically lifting from a sealed position on the interior surface of the rim of the canister to an uncompressed position on a top edge of the interior surface of the rim of the canister when a vacuum is not applied to the canister interior through the vacuum port by the vacuum source.

11. The system of claim 10 wherein the canister liner further includes an annular recess portion positioned between the sidewall and the annular tapered sealing surface.

12. The system of claim 11 wherein the canister liner further includes an annular transition portion positioned between the annular recess portion and the annular tapered sealing surface.

13. The system of claim 10 wherein the canister liner further includes a circumferential collar portion positioned above the annular tapered sealing surface.

14. The system of claim 13 wherein the canister liner further includes a circumferential lip portion positioned at a top edge of the circumferential collar portion.

15. The system of claim 13 wherein the plurality of protrusions are positioned between the circumferential collar portion and the annular tapered sealing surface.

16. The system of claim 15 wherein the canister liner further includes a step portion running between the plurality of protrusions.

17. The system of claim 13 wherein the canister liner further includes a step portion positioned between the circumferential collar portion and the annular tapered sealing surface.

18. The system of claim 10 wherein the canister liner further includes a step portion positioned over the annular tapered sealing surface.

* * * * *